United States Patent [19]
Housman

[11] Patent Number: 6,054,273
[45] Date of Patent: Apr. 25, 2000

[54] INHIBITORS OF ALTERNATIVE ALLELES OF GENES AS A BASIS FOR CANCER THERAPEUTIC AGENTS

[75] Inventor: David E. Housman, Newton, Mass.

[73] Assignee: Variagenics Inc., Cambridge, Mass.

[21] Appl. No.: 08/967,454

[22] Filed: Nov. 11, 1997

Related U.S. Application Data

[63] Continuation of application No. 08/379,680, Apr. 4, 1995, Pat. No. 5,702,890, which is a continuation-in-part of application No. PCT/US94/08473, Jul. 26, 1994, which is a continuation-in-part of application No. 08/095,597, Jul. 26, 1993, abandoned.

[51] Int. Cl.[7] .............................. C12Q 1/68; C12N 5/08
[52] U.S. Cl. ............................................. 435/6; 435/366
[58] Field of Search ............................ 424/130.1; 514/2, 514/44; 435/6, 366

[56] References Cited

FOREIGN PATENT DOCUMENTS

WO 93/17715    9/1993    WIPO.

OTHER PUBLICATIONS

Osband et al. (Jun. 1990) Problems in the investigational study and clinical use of cancer immunotherapy. Immunol. Today 11:193–195.
Hird et al. (1990) Immunotherapy with monoclonal antibodies. In "Genes and Cancer", D. Carney, K. Sikora (Eds.) John Wiley & Sons Ltd. pp. 183–189.
Harris et al. (Feb. 1993) Therapeutic antibodies–the coming of age. Trends Biotechnol. 11:42–44.
Branch (Feb. 1998) A good antisense molecule is hard to find. Trends Biol. Sci. 23:45–50.
Stull et al. (Apr. 1995) Antigene, ribozyme and aptamer nucleic acid drugs: progress and prospects. Pharm. Res. 12:465–483.
Rojanasakul (1996) Antisense oligonucleotide therapeutics: delivery and targeting. Adv. Drug Del. Rev. 18:115–131.
Gura (Nov. 1997) Systems for identifying new drugs are often faulty. Science 278:1041–1042.
Abbas, Lichtman and Pober, *Cellular and Molecular Immunology*, W.B. Saunders Co. (1991).
Bolis et al., "A Machine Learning Approach to Computer–Aided Molecular Design," *J. Computer–Aided Molecular Design* 5:617–628 (1991).
Buetler, E., *Clinical Biochemistry* 24:293–300 (1991).
Cameron and Jennings, "Specific gene suppression by engineered ribozymes in monkey cells," *PNAS USA* 86:9139–9143 (1989).
Coligan, J.E., et al. "Current Protocols in Immunology," Wiley Interscience, NY (1990).
Cooper, D. et al., *Human Genetics* 69:201–205 (1985).
Cotton and Birnstiel, "Ribozyme mediated destruction of RNA in vivo," *EMBO J.* 8:3861–3866 (1989).
Dixon, J., "Computer–aided Drug Design: Getting the Best Results," *Trends in Biotechnology*, 10:357–363 (1992).
Flach, J.E., et al., *Mol. Biol. Med.* 7:365–369 (1990).

Freshney, I.R., "Culture of Animal Cells: A Manual of Basic Technique," Alan R. Liss, Inc., NY, NY (1983).
Gerlach and Young, "ribozymes for the Control of Gene Activity in vivo," *Antisense Nucleic Acids and Proteins: Fundamentals and Applications,* edited by J.N.M. Mol & A.R. van der Drol. Marcel Kekker, Inc. NY, Chapter 8 (1990).
Harlow, E. and D. Lane, "Antibodies," Cold Spring Harbor Laboratory Press, Cold Spring Harbor, NY (1988).
Hilbert et al., "Receptor 3D–Models and Drug Design," *Therapie* (Paris) 46:445–451 (1991).
Holzmayer, T.A., et al., *Nucleic Acids Research* 20(4):711–717 (1992).
Inouye, Antisense RNA; its functions and applications in gene regulation—a review, *Gene* 72:25–34 (1988).
Keen, J., D. Lester, C. Inglehearn, A. Curtis and S. Bhattacharya, "Rapid Detection of Single Base Mismatches as Heteroduplexes on Hydrolink Gels," *Trends in Genetics* 7:5 (1991).
Klopman, G., "Multicase 1: A Hierarchical ComputerAutomated Structure Evaluation Program," *Quantitative Structure–Activity Relationships* 10:350–358 (1991).
Kuntz, I., "Structure–Based Strategies for Drug Design and Discovery," *Science* 257:1078–1082 (1992).
Lasko, D., et al., *Ann. Rev. Genetics* 25: 281–314 (1991).
Lawrence and Davis, "CLIX: A Search Algorithm for Finding Novel Ligands Capable of Binding Proteins of Known Three–Dimensional Structure," *Proteins Structure Functional Genetics* 12:31–41 (1992).
Masters and Attardi, "The nucleotide sequence of the cDNA coding for the human dihydrofolic acid reductase," *Gene* 21:59–63 (1983).
Masters et al., "A Human Dihydrofolatte Reductase Pseudogene and its Relationship to the Multiple Forms of Specific Messenger RNA," *J. Mol. Bio.* 167:23–36 (1983).
McCafferty, et al., *Nature* 348:552 (1990).

(List continued on next page.)

*Primary Examiner*—Robert A. Schwartzman
*Attorney, Agent, or Firm*—Lyon & Lyon LLP

[57] ABSTRACT

This invention is directed to a therapeutic strategy involving (1) identification of alternative alleles of genes coding for protein vital for cell viability or cell growth and the loss of one of those alleles in cancer cells due to loss of heterozygosity (LOH) and (2) the development of inhibitors with high specificity for the single remaining alternative allele of the vital gene retained by the cancer cell after LOH. The inhibitors of this invention are specific for one alternative allele of a gene that codes for a protein vital to cell viability or cell growth. The targeted gene has two alternative alleles in which the inhibitors of this invention blocks only one of the two alternative alleles, still present in the cancer cells. Exposure to the inhibitor inhibits or kills cancer cells which have undergone LOH. Protein is still capable of being expressed in the normal cells exposed to the inhibitor by the unblocked alternative allele. This differential effect of the inhibitor on cancer cells and normal cells accounts for the high therapeutic index of the inhibitors of this invention when used as antineoplastic agents.

2 Claims, No Drawings

OTHER PUBLICATIONS

McClelland, Kuhn & Ruddle, "The Human Transferrin Receptor Gene: Genomic Organization and the Complete Primary Structure of the Receptor deduced from a cDNA Sequence," *Cell* 39:267–274 (1994).

Miller and Ts'O, *Anti–Cancer Drug Des.* 2:11–128 (1987).

Mitelman, F., *Catalog of Chromosome Aberrations in Cancer* New York: Liss (1988).

Monia, et al., "Selective Inhibition of Mutant Ha–ras mRNA Expression by Antisense Oligonucleotides," *J. Biol. Chem.*, 267(28):19954–19962 (1992).

Morandni et al., "Multiple Forms of Human Dihydrofolate Reductase Messenger RNA," *J. Mol. Bio.* 156:583–607 (1982).

Myers, Maniatis, and Lerman, *Methods Enzymol.* 155:501–527 (1987).

Orita, et al., Rapid and Sensitive Detection of Point Mutations and DNA Polymorphisms Using the Polymerase Chain Reaction, *Genomics* 5:874–879 (1989).

Pelletier, J., et al., *Cell* 67:437–447 (1991).

Piper et al., "Studies Aided by Molecular Graphics of Effects of Structural Modifications on the Binding of Antifolate Inhibitors to Human Dihydrofolate Reductase," *Proc. Am. Assoc. Cancer Res. Annual Meeting* 33:412 (1992).

Sambrook, Fritsch, Maniatis, *Molecular Cloning, A Laboratory Manual,* Cold Spring Harbor Press, Cold Spring Harbor, NY p. 7.19–7.22 (1989).

Sandberg, *The Chromosomes in Human Cancer and Leukemia,* New York: Elsevier (1980).

Sato, J.K., et al., *Proceedings of AACR,* vol. 26, Abstract No. 903, p. 229 (1985).

Sato, J.K., et al., *Proceedings of AACR,* vol. 27, Abstract No. 1023, p. 258 (1986).

Schneider, C., et al., *Nature,* 311:675–678 (1984).

Scott, J.K. ans G.P. Smith, "Searching for Peptide Ligands with an Epitope Library," *Sciences,* 249:386–390 (1990).

Seizinger, B.R., et al., Cytogenet. *Cell Genetics,* 58: 1080–1096 (1991).

Silverman, R., *The Organic Chemistry of Drug Design and Drug Action,* Academic Press (1992).

Taetle, R., et al., *Cancer Research,* 46:1759–1763 (1986).

Testa, U., et al., *Normal and neoplastic Blood Cells:From Genes to Therapy,* Annals of the New York Academy of Sciences, 511:131–137 (1987).

Toulme and Helene, "Antimessenger oligodeoxyribonucleotides; an alternative to antisense RNS for artificial regulation of gene expression—a review," *Gene* 72:51–58 (1988).

Trojan, J., et al., *Science* 259:94–97 (1993).

Trowbridge, I.S., et al., *Proc. Natl. Acad. Sci., USA* 79:1175–1179 (1982).

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 19 amino acids
      (B) TYPE: amino acid
      (C) STRANDEDNESS: single
      (D) TOPOLOGY: linear (ii) MOLECULE TYPE: Peptide (ix) FEATURE:
      (D) OTHER INFORMATION: "Xaa" stands for Norleucine.

(xi) SEQUENCE DESCRIPTION: SEQ ID NO: 1:

Cys Xaa Lys Leu Asp Ser Thr Asp Phe Thr Ser Thr Ile Lys Leu Leu
1               5                   10                  15

Asn Glu Cys (2) INFORMATION FOR SEQ ID NO: 2:

(i) SEQUENCE CHARACTERISTICS:
      (A) LENGTH: 19 amino acids
      (B) TYPE: amino acid
      (C) STRANDEDNESS: single
      (D) TOPOLOGY: linear (ii) MOLECULE TYPE: Peptide (ix) FEATURE:
      (D) OTHER INFORMATION: "Xaa" stands for Norleucine.

(xi) SEQUENCE DESCRIPTION: SEQ ID NO: 2:

Cys Xaa Lys Leu Asp Ser Thr Asp Phe Thr Gly Thr Ile Lys Leu Leu
1               5                   10                  15

Asn Glu Cys (2) INFORMATION FOR SEQ ID NO: 3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO: 3:

GAGGTCCTCC CGCTGCTGTC                    20

(2) INFORMATION FOR SEQ ID NO: 4:

(i) SEQUENCE CHARACTERISTICS:
        (A) LENGTH:           21 base pairs
        (B) TYPE:             nucleic acid
        (C) STRANDEDNESS:     single
        (D) TOPOLOGY:         linear (xi) SEQUENCE DESCRIPTION: SEQ ID NO: 4:

CTTGAGTTCT CTGCTGAGAA C                  21

(2) INFORMATION FOR SEQ ID NO: 5:

(i) SEQUENCE CHARACTERISTICS:
        (A) LENGTH:           21 base pairs
        (B) TYPE:             nucleic acid
        (C) STRANDEDNESS:     single
        (D) TOPOLOGY:         linear (xi) SEQUENCE DESCRIPTION: SEQ ID NO: 5:

CATTCCTGAG AAGAATCGAC C                  21

(2) INFORMATION FOR SEQ ID NO: 6:

(i) SEQUENCE CHARACTERISTICS:
        (A) LENGTH:           21 base pairs
        (B) TYPE:             nucleic acid
        (C) STRANDEDNESS:     single
        (D) TOPOLOGY:         linear (xi) SEQUENCE DESCRIPTION: SEQ ID NO: 6:

GTCTTGCATG ATCCTTGTCA C                  21

(2) INFORMATION FOR SEQ ID NO: 7:

(i) SEQUENCE CHARACTERISTICS:
        (A) LENGTH:           19 base pairs
        (B) TYPE:             nucleic acid
        (C) STRANDEDNESS:     single
        (D) TOPOLOGY:         linear (xi) SEQUENCE DESCRIPTION: SEQ ID NO: 7:

GAAGCCATGA ATCACCCAG                     19

(2) INFORMATION FOR SEQ ID NO: 8:

(i) SEQUENCE CHARACTERISTICS:
        (A) LENGTH:           21 base pairs
        (B) TYPE:             nucleic acid
        (C) STRANDEDNESS:     single
        (D) TOPOLOGY:         linear (xi) SEQUENCE DESCRIPTION: SEQ ID NO: 8:

CTTAAACTAG AAAACACCTT C                  21

(2) INFORMATION FOR SEQ ID NO: 9:

(i) SEQUENCE CHARACTERISTICS:
        (A) LENGTH:           20 base pairs
        (B) TYPE:             nucleic acid
        (C) STRANDEDNESS:     single
        (D) TOPOLOGY:         linear (xi) SEQUENCE DESCRIPTION: SEQ ID NO: 9:

```
GTACAAATTT GAAGTATATG                                                      20

(2) INFORMATION FOR SEQ ID NO: 10:

(i) SEQUENCE CHARACTERISTICS:
        (A) LENGTH:            20 base pairs
        (B) TYPE:              nucleic acid
        (C) STRANDEDNESS:      single
        (D) TOPOLOGY:          linear (xi) SEQUENCE DESCRIPTION: SEQ ID NO: 10:

GGTCTTGGAG AAGCACTTAG                                                      20

(2) INFORMATION FOR SEQ ID NO: 11:

(i) SEQUENCE CHARACTERISTICS:
        (A) LENGTH:            20 base pairs
        (B) TYPE:              nucleic acid
        (C) STRANDEDNESS:      single
        (D) TOPOLOGY:          linear (xi) SEQUENCE DESCRIPTION: SEQ ID NO: 11:

CATTTATGAG ACATTCTTGC                                                      20

(2) INFORMATION FOR SEQ ID NO: 12:

(i) SEQUENCE CHARACTERISTICS:
        (A) LENGTH:            20 base pairs
        (B) TYPE:              nucleic acid
        (C) STRANDEDNESS:      single
        (D) TOPOLOGY:          linear (xi) SEQUENCE DESCRIPTION: SEQ ID NO: 12:

GCTTTTGGTA TTTCCACTAG                                                      20
```

INHIBITORS OF ALTERNATIVE ALLELES OF GENES AS A BASIS FOR CANCER THERAPEUTIC AGENTS

This is a continuation of application Ser. No. 08/379,680 filed Apr. 4, 1995 U.S. Pat. No. 5,702,890, which is a national stage application under 35 U.S.C. 0371 of International Application Ser. No. PCT/US94/08473, filed Jul. 26, 1994, which is a continuation-in-part of U.S. application Ser. No. 08/095,597, filed Jul. 26, 1993 abandoned, hereby incorporated by reference in their entireties (including drawings).

FIELD OF THE INVENTION

This application is directed to therapeutic inhibitors to treat cancer and strategies for the development of cancer treatments having a high therapeutic index.

BACKGROUND OF THE INVENTION

The targeting of chemotherapeutic agents to tumor cells is one of the most heavily investigated areas in biomedical research today. Although effective antineoplastic agents have been and continue to be discovered, there remains the immense problem of targeting these highly toxic agents specifically to tumor cells so that they do not also kill normal somatic cells and thereby cause permanent damage to vital organs or even death. Indeed, one measure of the clinical usefulness of any antineoplastic agent is its therapeutic index: the ratio of the median lethal dose ($LD_{50}$) to the median effective dose ($ED_{50}$) of the drug. With some cancer therapeutics this ratio is close to one, indicating a high level of toxic side effects to the patient.

SUMMARY OF THE INVENTION

Cancer cells almost invariably undergo a loss of genetic material (DNA) when compared to normal cells. This deletion of genetic material is technically referred to as "loss of heterozygosity" (LOH). Recognizing that almost all, if not all, varieties of cancer undergo LOH, and that these regions are quite extensive, the inventor evaluated the genetic content of deleted regions in cancer cells and realized that genes vital for cell viability or cell growth are frequently deleted. Further investigation has culminated in the discovery that the loss of genetic material from cancer cells sometimes results in the selective loss of one of two alleles of a certain vital gene at a particular locus on the chromosome. Based on this analysis, the inventor has devised a unique therapeutic strategy for the treatment of cancer. This strategy will result in agents characterized by a high therapeutic index. The strategy includes (1) identification of alternative alleles of genes coding for proteins vital for cell viability or growth; (2) identification of the absence of one of these alleles in cancer cells and (3) development of specific inhibitors of the single remaining allele of the vital gene retained by the cancer cell after LOH.

The inhibitors described in this invention are specific for one allele of a gene that codes for a protein vital to cell growth or cell viability. Exposure to the inhibitor inhibits proliferation or kills cancer cells which have undergone genetic deletion such that the cells only express the single allelic form of the vital protein against which the inhibitor is targeted. Normal cells exposed to the inhibitor are spared from the toxic effects of the inhibitor because the remaining activity of the unblocked alternative allele is adequate to permit continued cell viability and growth. This differential effect of the inhibitor on cancer cells and normal cells accounts for the high therapeutic index of the inhibitors of this invention when used as antineoplastic agents. Toxicity of the inhibitor to normal cells is therefore low, compared to most currently available antineoplastic agents.

DETAILED DESCRIPTION OF THE INVENTION

I. Introduction

All genes, except those of the two sex chromosomes, exist in duplicate in human cells, with one copy of each gene (allele) found at the same place (locus) on each of the paired chromosomes. Each chromosome pair thus contains two alleles for any gene—one from each parent. This redundancy of allelic gene pairs on duplicate chromosomes provides a safety system; if a single allele of any gene pair is defective or absent, the surviving allele will continue to produce the coded protein.

Because humans are genetically heterogeneous, technically referred to as DNA polymorphism, many of the paired alleles of genes differ from one another. When the two alleles are identical, the individual is said to be homozygous for that pair of alleles at that particular locus. Alternatively, when the two alleles are different, and usually the differences are small, the individual is heterozygous at that locus. Typically both alleles are transcribed and ultimately translated into proteins used by the cell.

In the homozygous situation both alleles are identical, hence proteins encoded by the two alleles are identical. In the heterozygous situation, each allele encodes a different mRNA. Depending on the effect of the nucleotide difference on the relevant codon, the mRNAs encoded by two alleles may translate into the same protein or into forms of the same protein differing by one or more amino acids. If one of a pair of heterozygous alleles is lost due to a deletion of DNA from one of the paired chromosomes, only the remaining allele will be expressed and the affected cells will be functionally homozygous. This situation is termed a "loss of heterozygosity" (LOH) or reduction to homozygosity. Following this loss of an allele from a heterozygous cell, the protein or gene product thereafter expressed will be homogeneous because all of the protein will be encoded by the single remaining allele. The cell becomes effectively homozygous at the gene locus where the deletion occurred. Almost all, if not all, cancer cells undergo LOH at some chromosomal regions.

The inventor recognized that a therapeutic strategy can be designed around the loss of heterozygosity (LOH) in cancer cells if this loss occurs in a gene expressing a protein which is necessary for cell viability or growth. This strategy begins with the identification of heterozygous alleles of genes coding for proteins essential for cell viability or growth in normal cells and the loss of one of the allele in cancer cells. Mitelman, F., *Catalog of Chromosome Aberrations in Cancer*, New York: Liss (1988); Sandberg, *The Chromosomes in Human Cancer and Leukemia*, New York: Elsevier (1980); Seizinger, et al., "Report of the committee on chromosome and gene loss in neoplasia," *Cytoaenet. Cell Genetics*, 58:108–1096 (1991).

Through the use of DNA probes, DNA from an individual's normal cells can be compared with DNA extracted from the same individual's tumor cells. LOH can be identified when Southern blot hybridization analysis reveals heterozygosity (dissimilar alleles) of a gene in the normal cells but homozygosity (identical alleles) of the same gene in the tumor cells. Alternatively, LOH can be assayed by demonstrating two polymorphic forms of a protein in normal heterozygous cells, and only one form in cancer cells where the deletion of an allele has occurred. A review of many published studies of LOH in cancer cells is described in Lasko, Cavenee, and Nordenskjold, "Loss of Constitutional Heterozygosity in Human Cancer," *Ann. Rev. Genetics*, 25:281–314 (1 991).

The alternative alleles of genes coding for proteins vital for cell viability or growth are termed herein "allele A" and "allele B." Typically the loss of a single copy of any gene pair, either allele A or allele B, is not fatal. The surviving copy is able to maintain normal cell function by continuing to express the vital protein. Transformed cancer cells, in which one allele of a gene encoding a vital protein has been deleted, are similarly still capable of producing the protein from the remaining allele. If allele B is lost due to LOH in a tumor cell, allele A still functions. However, if this tumor cell, which has only the A allelic form of the protein left, is treated with an inhibitor directed specifically to allele A, the cell will cease growth or die because either the synthesis of the vital protein or its biological activity will be suppressed by exposure to the inhibitors of this invention.

This same allele A-specific inhibitor which is fatal to the cancer cell will not kill a normal cell with two functioning alleles, A and B. The gene product produced from allele A will be inhibited in normal cells, but allele B will be unaffected and will continue to produce the vital protein, permitting normal cells to survive.

This invention is thus directed to the therapeutic use of inhibitors directed at one allele of a pair of alleles encoding a protein vital to cell growth. Various types of inhibitors can be identified which affect the function of the vital protein, or alternatively inhibit the transcription or translation of one of the alternative alleles. The result of the inhibition is a selective decrease in gene activity by specific inhibition of one allelic form of the protein.

The "inhibitors" or "antineoplastic agents" of this invention represent a new approach to cancer therapy because they are lethal only for cancer cells. The advantages of this approach include, first, lack of toxicity to the normal cells of the patient resulting in a therapeutic index greater than that of conventional cancer chemotherapy drugs, and second, it is not necessary that the inhibitors be targeted specifically to the cancer cells, as they can be administered systemically.

The strategy to be applied in cancer therapy is as follows: (1) the identification in a cancer patient of heterozygous loci (with alleles A and B) coding for proteins vital for cell viability and/or cell growth; (2) the identification of the loss or the absence of one of the alleles in cancer cells due to genetic deletion and (3) the applications of inhibitors with high specificity for the single remaining allele of the vital gene retained by the cancer cell after LOH.

Normal cells expressing equal amounts of allele A and allele B of the vital gene will typically show a reduction in gene activity when they take up the inhibitors of this invention, but should remain viable due to the activity of the protein encoded by the uninhibited allele. On the other hand, cancer cells expressing only one allele due to LOH, either allele A or allele B, will respond to the inhibitors of this invention which are specifically directed to the remaining allele, with a substantial reduction in gene activity. Growth of cancer cells exposed to the inhibitors of this invention will be inhibited due to the suppression of either the synthesis or the biological activity of the vital gene product. To have a high therapeutic index, an inhibitor should selectively block the activity of one allele, for example the allele A form, but have no inhibitory effect on the activity of the allele B form.

One gene can have only two allelic forms in any given individual, but a gene can have more than two alleles in the human population. According to this invention, inhibitors can be targeted to any of the alleles in the population. Thus, this invention is directed to an inhibitor with a specificity for an allele of a gene coding for a protein vital for cell viability or cell growth, where the gene has two or more alleles in the human population.

II. Identification of Alternative Alleles

The cancer therapy strategy of this invention utilizes the genetic differences between normal cells and cancer cells. The first step in the therapeutic strategy is identifying genes which code for proteins or other factors vital to cell survival and growth that are lost through LOH in cancer cells. Since many genes have been mapped to specific chromosomal regions, this search is best started by investigating the chromosomal regions characteristically deleted in different forms of human cancer. Table 1 from the review conducted by Lasko et al. in *Ann. Rev. Genetics*, supra, summarizes results of numerous studies determining loss of heterozygosity in tumors.

Once sites of deletions are identified in the chromosomes of a patient's cancer cells, genes which map to the deleted chromosomal segments and are known to code for proteins vital for cell growth or survival will be tested for DNA polymorphism. The goal is to identify all sites of LOH in the chromosomes of the cancer cells to afford the broadest selection of target genes coding for vital proteins.

TABLE 1

| Loss of Heterozygosity in Human Solid Tumors | |
|---|---|
| Chromosome Region | Tumor Type |
| 1p | Breast carcinoma |
| | Cutaneous melanoma (metastastic) |
| | Medullary thyroid carcinoma: MEN2A |
| | Neuroblastoma |
| | Pheochromocytoma: MEN2A sporadic |
| 1q | Breast carcinoma |
| | Gastric adenocarcinoma |
| 2 | Uveal melanoma |
| 3p | Breast carcinoma |
| | Cervical carcinoma |
| | Lung cancer: |
| | small carcinoma |
| | non-small cell carcinoma |
| | large cell carcinoma |
| | squamous cell carcinoma |
| | adenocarcinoma |
| | Ovarian carcinoma |
| | Renal cell carcinoma: familial sporadic |
| | Testicular carcinoma |
| 4q | Hepatocellular carcinoma |
| 5q | Colorectal carcinoma |
| | Hepatocellular carcinoma |
| 6q | Ovarian carcinoma |
| | Primitive neuroectodermal tumor |
| | Renal cell carcinoma |
| | Testicular teratocarcinoma |
| 9p | Glioma |
| 9q | Bladder carcinoma |
| 10 | Glioblastoma multiforme |
| 10q | Hepatocellular carcinoma |
| | Prostate cancer |

TABLE 1-continued

Loss of Heterozygosity in Human Solid Tumors

| Chromosome Region | Tumor Type |
|---|---|
| 11p | Adrenal adenoma |
|  | Adrenocortical carcinoma |
|  | Bladder carcinoma |
|  | Breast carcinoma |
|  | Embryonal rhabdomyosarcoma |
|  | Hepatoblastoma |
|  | Hepatocellular carcinoma |
|  | Lung cancer: |
|  | squamous cell carcinoma |
|  | large cell carcinoma |
|  | adenocarcinoma |
|  | Ovarian carcinoma |
|  | Pancreatic cancer |
|  | Parathyroid tumors |
|  | Pheochromocytoma |
|  | Skin cancer |
|  | squamous cell carcinoma |
|  | basal cell carcinoma |
|  | Testicular cancer |
|  | Wilms tumor |
| 11q | Insulinoma |
|  | Parathyroid tumors |
| 12q | Gastric adenocarcinoma |
| 13q | Adrenocortical adenoma |
|  | Breast carcinoma |
|  | Gastric carcinoma |
|  | Hepatocellular carcinoma |
|  | Lung cancer: |
|  | small cell carcinoma |
|  | Neuroblastoma |
|  | Osteosarcoma |
|  | Retinoblastoma |
| 14 | Colorectal carcinoma |
| 14q | Neuroblastoma |
| 16 | Breast carcinoma |
| 16q | Breast carcinoma |
|  | Hepatocellular carcinoma |
|  | Primitive neuroectodermal tumor |
|  | Prostate cancer |
| 17p | Adrenocortical adenoma |
|  | Astrocytoma |
|  | Bladder carcinoma |
|  | Breast carcinoma |
|  | Colorectal carcinoma |
|  | Lung cancer: |
|  | small cell carcinoma |
|  | squamous cell carcinoma |
|  | adenocarcinoma |
|  | Medulloblastoma |
|  | Neurofibrosarcoma: NF1 |
|  | Osteosarcoma |
|  | Ovarian carcinoma |
|  | Primitive neuroectodermal tumor |
|  | Rhabdomyosarcoma |
| 17q | Breast carcinoma |
|  | Neurofibroma: NF1 |
| 18 | Renal cell carcinoma |
| 18q | Breast carcinoma |
|  | Colorectal carcinoma |
| 22q | Acoustic neurinoma |
|  | Colorectal carcinoma |
|  | Ependymoma |
|  | Meningioma |
|  | Neurofibroma |

There are three basic criteria for selecting these genes: (1) the locus coding for the vital protein must be heterozygous, i.e., there must be two or more allelic forms in the human population; (2) the heterozygous alleles must differ in a way that permits the design of an allele-specific inhibitor, which may target DNA, RNA, or protein differences; and, (3) the targeted locus must encode a protein necessary for cell growth or survival so that inhibition of the gene or its product will either reduce cell division or cell growth or kill the cell.

As used herein the term, "genes which code for proteins or factors required for cell viability" is meant to include those genes that express proteins required for cell survival as well as those genes required for cell growth in actively dividing cell populations. These genes encode proteins which can be involved in any vital cell process such as, but not limited to, DNA replication, gene transcription and translation, intracellular or transmembrane transport, regulation of transcription or translation, cellular energy metabolism, DNA repair, mitosis, signal transduction, or regulation of these functions.

One illustration is the transferrin receptor (TFRC). All actively dividing cells need iron for their growth and to sustain essential metabolic pathways. Iron is required for a large number of cellular enzymes, including cytochromes, which are necessary for oxidative phosphorylation and for ribonucleotide reductase, the enzyme catalyzing conversion of ribonucleotides to deoxyribonucleotides. The transferrin receptor participates in the cellular acquisition of iron from transferrin by receptor mediated endocytosis. The receptor is expressed on virtually all human cells. It is composed of two identical subunits held together by disulfide bonds to form a dinner of 180 kilodaltons. The gene encoding the transferrin receptor is located on chromosome 3 (q26.2-q-ter), a chromosome which frequently undergoes loss of heterozygosity in a variety of cancers including small cell lung cancer and adult kidney cancer. All or part of chromosome 3 is deleted in virtually 100% of small cell lung cancer; in >90% of renal cancers; in ~50% of all non small cell lung cancer; in ~50% of cervical carcinomas; and in ~40% of all breast cancers. This is probably due to the fact that several tumor suppressor genes are encoded on chromosome 3.

Another illustration is human dihydrofolate reductase (DHFR). The antifolates are a class of potent antimetabolites. Methotrexate (MTX) is the most widely used antifolate in cancer therapy. It inhibits dihydrofolate reductase, which maintains the intracellular folate pool in the form of tetrahydrofolate. The reduction of folic acid to its active form, tetrahydrofolate, occurs in two steps, in which two successive pairs of hydrogen atoms are added. The second step is catalyzed by dihydrofolate reductase. Tetrahydrofolate is an essential co-enzyme for the de novo synthesis of pyrimidines and purines. The reaction catalyzed by DHFR is crucial for the biosynthesis of pyrimidines and purines since there exists no redundancy in this pathway. Thus, inhibition of DHFR by methotrexate leads to cell killing.

Once a gene coding for a protein or factor vital to cell viability is identified, its genomic DNA and cDNA sequences, if not previously established, can be ascertained and sequenced according to standard techniques. Sambrook, Fritsch and Maniatis, "Molecular Cloning, A Laboratory Manual," Cold Spring Harbor Press, Cold Spring Harbor, N.Y. (1989). The next step is to test DNA from multiple individuals to determine whether the DNA sequence for the target gene is polymorphic. The target gene of this invention must occur as heterozygous alleles in the population; that is, the DNA polymorphism should either affect the primary amino acid sequence of the product of the targeted gene, which would facilitate the design of inhibitors of the protein product, or be a mutation anywhere within the genomic DNA sequence, including the promoter or intron regions, such that it can be exploited to design inhibitors of transcription or translation which distinguish between the two heterozygous alleles of the targeted gene. Polymorphisms that do not alter protein sequence can be targeted with antisense oligonucleotides.

The most elementary genetic variant, which is common in mammalian genomes, is the single nucleotide substitution. It has been estimated that the comparison of haploid genomes will reveal this type of variant every 300 to 500 nucleotides (Cooper, et al., *Human Genetics* 69:201:205 (1985)). The most common technique currently employed in the identification of such single nucleotide polymorphisms is single strand conformation polymorphism (SSCP) method. (Orita, et al., "Rapid and Sensitive Detection of Point Mutations and DNA Polymorphisms Using the Polymerase Chain Reaction, *Genomics,* 5:874–879 (1989)). Also employed are restriction fragment length polymorphism (RFLP), heteroduplex analysis, ligase chain reaction (LCR), denaturing gradient gel electrophoresis (DGGE) (Myers, Maniatis, and Lerman, *Methods Enzymol.,* 155:501–527 (1987)) or direct nucleotide sequencing. The SSCP method reveals the presence of sequence variation between individuals as shifts in electrophoretic mobility, but does not show the sequence itself. Direct sequencing of DNAs with altered mobility will identify the precise nucleic acid sequence differences among the various alleles. From the nucleic acid sequence data, the amino acid sequence can be determined. One example of the use of this technique is in Pelletier et al. *Cell,* 67:437–447 (1991).

III. Inhibitors for the Alternative Alleles

Once two or more alleles are identified for the target vital gene, inhibitors of high specificity for the protein product of either allele A or B can be designed or identified empirically. As used herein, the term "inhibitors" is meant to include any molecule or compound capable of allele-specific blocking of transcription or translation or of allele specific inhibition of the activity performed by the vital protein.

Inhibitors that can be used in the present invention will depend on whether allelic variation at a target locus affects the amino acid sequence, the mRNA sequence, or the DNA in intron and promoter regions. If there is variation at the protein level, then classes of inhibitors to consider would include targeted low molecular weight drugs, oligopeptides and their derivatives, and antibodies, including modified or partial antibody fragments or derivatives. For mRNA or DNA polymorphism the main class of inhibitors are complementary oligonucleotides and their derivatives and catalytic RNA molecules such as ribozymes. The generation of inhibitors of this invention can be accomplished by a number of methods. The preferred method for the generation of specific inhibitors of the targeted allelic gene product relies on computer modeling of both the target protein and the specific inhibitor. Other methods include screening compound libraries or microorganism broths, empirical screening of libraries of peptides displayed on bacteriophage, and various immunological approaches. Further, in the treatment of cancer patients, a therapeutic strategy includes using more than one inhibitor of this invention to inhibit more than one target. In this manner, inhibitors directed to different proteins vital to cell growth can be targeted and inhibited simultaneously. The advantage of this approach is to increase the specificity of the inhibition of proliferation of cancer cells, while at the same time maintaining a low incidence of side effects.

A. Targeted Drug Design

Computer-based molecular modeling of target proteins encoded by the various alleles can be used to predict their three-dimensional structures using computer visualization techniques. On the basis of the differences between the three-dimensional structure of the alternate allelic forms of the proteins, determinants can be identified which distinguish the allelic forms. Novel low molecular weight inhibitors or oligopeptides can then be designed for selective binding to these determinants and consequent allele-specific inhibition. Descriptions of targeted drug design can be found in I. Kuntz, "Structure-Based Strategies for Drug Design and Discovery," *Science,* 257:1078–1082 (1992) and J. Dixon, "Computer-Aided Drug Design: Getting the Best Results," *Trends in Biotechnology,* 10:357–363 (1992). Specific applications of the binding of molecules to receptors using computer modeling have been described in Piper et al., "Studies Aided by Molecular Graphics of Effects of Structural Modifications on the Binding of Antifolate Inhibitors to Human Dihydrofolate Reductase," *Proc Am. Assoc. Cancer Res. Annual Meeting,* 33:412 (1992); Hibert et al., "Receptor 3D-Models and Drug Design," *Therapie* (Paris), 46:445–451 (1991)(serotonin receptor recognition sites). Computer programs that can be used to conduct three-dimensional molecular modeling are described in G. Klopman, "Multicase 1: A Hierarchical Computer Automated Structure Evaluation Program," *Quantitative Structure-Activity Relationships,* 11:176–184 (1992); Pastor et., "The Edisdar Programs Rational Drug Series Design," *Quantitative Structure-Activity Relationships,* 10:350–358 (1991); Bolis et al., "A Machine Learning Approach to Computer-Aided Molecular Design," *J. Computer Aided Molecular Design,* 5:617–628 (1991); and Lawrence and Davis, "CLIX: A Search Algorithm for Finding Novel Ligands Capable of Binding Proteins of Known Three-Dimensional Structure," *Proteins Structure Functional Genetics,* 12:31–41 (1992).

Low molecular weight inhibitors specific for each allelic protein form can be predicted by molecular modeling and synthesized by standard organic chemistry techniques. Computer modeling can identify oligopeptides which block the activity of the product of the target gene. Techniques for producing the identified oligopeptides are well known and can proceed by organic synthesis of oligopeptides or by genetic engineering techniques. R. Silverman, *The Organic Chemistry of Drug Design and Drug Action,* Academic Press (1992).

The inhibitors of this invention can be identified by selecting those inhibitors that selectively inhibit the growth of cells expressing the B allelic form for example, but do not inhibit the activity of the A allelic form.

B. Antibody Inhibition

Once a vital gene is identified and is determined to exist in two or more allelic forms which encode different proteins, antibodies can be raised against both allelic forms of the protein. The techniques for using a specific protein or an oligopeptide as an antigen to elicit antibodies which specifically recognize epitopes on the peptide or protein are well known.

In one embodiment, the DNA sequence of the desired allelic form of the target gene can be cloned by insertion into an appropriate expression vector and translated into protein in a prokaryotic or eukaryotic host cell. The protein can be recovered and used as an antigen to elicit the production of specific antibodies. In another embodiment, the DNA of the desired allelic form of the target gene is amplified by PCR technology and is subsequently translated in vitro into protein to be used as the antigen to elicit the production of specific antibodies. A third embodiment is to use the DNA sequence of the alternative alleles as a basis for the generation of synthetic peptides representing the amino acid sequence of the alleles for use as antigen to elicit the production of specific antibodies.

Antibodies can be generated either by standard monoclonal antibody techniques or generated through recombinant based expression systems. See generally, Abbas, Lichtman, and Pober, *Cellular and Molecular Immunology*, W. B. Saunders Co. (1991). The term "antibodies" is meant to include intact antibody molecules of the IgD isotype as well as antibody fragments or derivatives, such as Fab and F(ab')2, which are capable of specifically binding to antigen. The antibodies so produced will recognize only the protein produced in the allelic form which was used as an antigen to create the antibody. If the antibody was elicited by exposure to the B form of the protein, and the B form is significantly different from the A form, then the antibody will bind only the B form. If the targeted protein is expressed on the cell surface, the antibody or antibody derivative can be tested as a therapeutic. Thus, if a cancer cell has undergone LOH due to selective loss of the A allele such that it now only expresses the B form of the vital protein, treatment with anti-B antibody will kill the cancer cell, or suppress proliferation. Normal cells, which express both the A and B forms of the vital protein, will lose the activity of the B form when treated with anti-B antibody, but they will survive because they can still utilize the A form of the protein which is not recognized by the antibody.

Antibody inhibitors are most effective when they are directed against cell surface proteins or receptors. If the vital protein produced by the targeted allele is not a cell surface protein or receptor, the development of antibody inhibitors may also require a special antibody-delivery system to facilitate entry of the antibody into the tumor cells. The plasma membrane that surrounds all cells is designed to limit the entrance of most compounds. Entry is generally restricted to small, non-charged molecules (absence of charge allows them to slip through the fatty membrane) or to those factors that can penetrate the cell using existing, specialized import mechanisms. The introduction into cells of much larger molecules, such as specific antibodies, other proteins, or peptides, will require appropriate delivery systems that are known in the art. Alternatively, the structure of the variable region of allele specific antibodies can be used as the basis for design of smaller allele specific inhibitory molecules.

C. Complementary Oligonucleotides, Oligopeptides, Ribozymes, and Other Low Molecular Weight Inhibitors Oligopeptides can be demonstrated to have a very high degree of specificity in their interaction with functional polypeptides such as cellular enzymes, receptors or other polypeptides essential for cell viability. Methods for screening peptide sequences which have high specificity for binding to, and functional inhibition of, a specific polypeptide target have been well described previously. Scott, J. K. and Smith G. P., "Searching for Peptide Ligands with an Epitope Library," *Science*, 249:386–390 (1990). These methods include the screening of M13 libraries by "phage display" of polypeptide sequences as well as direct screening of peptides or mixtures of synthetic peptides for binding to or inhibition of the target functional polypeptide. The oligopeptides of this invention can be synthesized chemically or through an appropriate gene expression system. Synthetic peptides can include both naturally occurring amino acids and laboratory synthesized, modified amino acids.

Oligonucleotides or oligonucleotide analogs which interact with complementary sequences of cellular target DNA or RNA can be synthesized and used to inhibit or control gene expression at the levels of transcription or translation. The oligonucleotides of this invention can be either oligodeoxyribonucleotides or oligoribonucleotides, or derivatives thereof, which are complementary to the allelic forms of the targeted vital gene or they can act enzymatically, such as ribozymes. Both antisense RNA and DNA can be used in this capacity as chemotherapeutic agents for inhibiting gene transcription or translation. Trojan, J., et al., "Treatment and prevention of rat glioblastoma by immunogenic C6 cells expressing antisense insulin-like growth factor I RNA," *Science*, 259:94–97 (1993). Inhibitory complementary oligonucleotides may be used as inhibitors for cancer therapeutics because of their high specificity and lack of toxicity.

Oligopeptides and other low molecular weight inhibitors can be identified and generated by at least one of the following methods: (1) phage display to identify peptides which bind to different allelic forms; (2) direct screening of peptide mixtures using a cDNA library; (3) screening of small organic molecules present in microorganism fermentation broth for allele-specific activity; or (4) screening of compound libraries.

A specific application of generating inhibitors which are either complementary oligonucleotides or inhibitory oligopeptides is described in Holzmayer, Pestov, and Roninson, "Isolation of dominant negative mutants and inhibitory antisense RNA sequences by expression selection of random DNA fragments," *Nucleic Acids Research*, 20:711–717 (1992). In this study, genetic suppresser elements (GSEs) are identified by random DNA fragmentation and cloning in expression plasmids.

Preferred oligonucleotide inhibitors include oligonucleotide analogues which are resistant to degradation or hydrolysis by nucleases. These analogues include neutral, or nonionic, methylphosphonate analogues, which retain the ability to interact strongly with complementary nucleic acids. Miller and Ts'O, *Anti-Cancer Drug Des.*, 2:11–128 (1987). Further oligonucleotide analogues include those containing a sulfur atom in place of the 3'-oxygen in the phosphate backbone.

The references cited herein are incorporated by reference for their disclosure of published laboratory techniques. The invention is illustrated further by the following examples, which are not to be taken as limiting in any way.

EXAMPLE A

The steps to execute this strategy are as follows:

1. Identify by appropriate DNA based biochemical techniques the sites of additional frequent nucleic acid and/or amino acid variation in the gene vital for cell growth in the human population.

2. Express variant forms of the protein encoded by the gene vital for cell growth in a prokaryotic or eukaryotic expression system in a manner that permits selection and/or screening for cells expressing gene activity as well as selection or screening for cells in which the gene activity has been blocked by an inhibitor. This system is then used to identify inhibitors which have a high degree of specificity for one allele form of the gene over another.

3. Once these inhibitors are identified, their effectiveness in arresting (inhibiting) cell growth or causing cell death is assayed on human cells of the appropriate genotypes to test for specificity. This initial test is followed by tests of cell killing or arresting in tumor cell lines of appropriate genotypes to test relative efficacy of the inhibitors in tumor cells. Demonstration of efficacy in cell killing in cultured tumor cell lines is followed by assessment of efficacy of an inhibitor in experimental tests in animal models of human tumors such as human tumor xenografts in nude or scid mice.

4. A successful outcome of the cultured cell work in step 3 permits the initiation of clinical trials. Patients' somatic cells and tumor cells are tested to determine alleles at the target gene locus. Patients are selected for treatment if their normal cells are heterozygous for the appropriate alleles and their tumors are homozygous for the gene due to LOH at the gene locus. These patients are given systemic doses of the allele specific inhibitor. A significant reduction of tumor burden compared to untreated control animals is an indication of a successful result.

EXAMPLE B

Transferrin Receptor (TFRC)

The basic principle which this example illustrates is the use of allele-specific antibodies against a polymorphic cell surface protein whose normal function is essential for cell growth. The gene encoding transferrin receptor is located on chromosome 3, one copy of which is frequently deleted in a variety of cancers, as described above. The activity of the transferrin receptor is essential for cell growth since it is the major route by which cells acquire iron, a vital element used by a number of cellular enzymes. Barnes, D. and Sato, G., "Methods for growth of cultured cells in serum free medium," *Analytical Biochemistry* 102:255–270 (1980). Direct evidence that transferrin receptor is vital for cell growth is provided by studies in which inhibition of this receptor by monoclonal antibodies leads to arrest of cell division. Trowbridge, I. and F. Lopez, "Monoclonal Antibody to transferrin receptor blocks transferrin binding and inhibits tumor cell growth in vitro," *Proc. Natl. Acad. Sci. USA* 79:1175–1179 (1982); Neckers, L. M. and J. Cossman, "Transferrin receptor induction in mitogen stimulated human T lymphocytes is required for DNA synthesis and cell division and is regulated by interleukin 2," *Proc Natl Acad Sci USA* 80:3494–3498 (1983).

1. Scanning the TFRC Gene for Polymorphic Differences that Alter the Encoded Amino Acid Sequence in the Extracellular Domain (Amino Acids 90–760).

The TFRC cDNA sequence has previously been determined. The two published sequences of transferrin receptor are identical over the entire protein coding sequence. Schneider, Owen, Banville & Williams "Primary structure of Human Transferrin Receptor Deduced from the mRNA Sequence," *Nature* 311:675–678 (1984); McClelland, Kuhn & Ruddle, "The Human Transferrin Receptor Gene: Genornic Organization and the Complete Primary Structure of the Receptor deduced from a cDNA Sequence," *Cell* 39:267–274 (1994).

To investigate the possible existence of variant alleles of TFRC we screened 39 human cell lines derived from normal lymphocytes (7) and a variety of tumor cell lines (32) for variation in the TFRC extracellular domain. Two standard techniques for detecting DNA sequence variation, single strand conformation polymorphism (SSCP) and heteroduplex analysis, were used to screen TFRC cDNA produced from each of the cell lines. The screening protocol consisted of 5 steps: a) isolate RNA from each of the cell lines; b) produce cDNA from each of the RNA samples; c) from each cDNA sample amplify DNA encoding the extracellular domain of the TFRC in 10 separate overlapping polymerase chain reaction (PCR) products using oligonucleotide primers specific for TFRC. (See Table below summarizing details of TFRC PCR primers and products.); d) use specialized electrophoretic techniques (SSCP and heteroduplex analysis) to analyze all PCR products, looking for altered electrophoretic mobility that would indicate the likely existence of sequence variants; e) sequence electrophoretic variant PCR products to determine nucleotide sequence of alternate alleles.

| TFRC PCR Products | | |
|---|---|---|
| Primer Pair | Bases Covered* | Size of Fragment Produced |
| T1–T2: | 501–743 | 243 bp |
| T3–T4: | 689–935 | 247 bp |
| T5–T6: | 886–1136 | 251 bp |
| T7–T8: | 083–1333 | 251 bp |
| T9–T10: | 1282–1533 | 252 bp |
| T11–T12: | 1476–1733 | 258 bp |
| T13–T14: | 1683–1920 | 238 bp |
| T15–T16: | 1870–2117 | 248 bp |
| T17–T18: | 2064–2321 | 258 bp |
| T19–T20: | 2269–2569 | 301 bp |

*Numbering of bases is from Schneider, et al. (cited above).

Using the strategy described, we detected two DNA polymorphisms in TFRC. The first polymorphism is at nucleotide 687 (again, numbering of bases from Schneider, Owen, Banville & Williams) and was detected in the 243 bp product produced with primers T1 and T2 (see table above). The published sequences indicate A; we found a second class of alleles with G at this position. The substitution of G for A changes codon 142 of TFRC from AGC, which encodes the amino acid serine, to GGC, which encodes glycine. Thus, the two alleles encode different versions of the TFRC protein. The substitution of G for A at nucleotide 687 also results in a new site for the restriction endonuclease Msp I, which recognizes and cleaves the sequence CCGG (but not CCAG). This difference in the DNA restriction pattern of the two alleles provides the basis for a simple test for determining an individual's genotype (see below). The second polymorphism is at nucleotide 2387 (third position of codon 708) and was detected in the 301 bp product produced with primers T19 and T20. The published sequences indicate G at this position. We found a new class of alleles with A, which does not alter the amino acid specified by codon 708 (both ACG and ACA encode threonine). The substitution of A for G eliminates a site for the restriction endonuclease BsoF1. This difference in the DNA restriction pattern of the two alleles provides the basis for a test to determine an individual genotype.

The results of screening our sets of human samples to determine the allele frequencies at these two positions are summarized in the Tables 3 and 4 below.

TABLE 3

| Genotype at position 687/codon 142 | | | |
|---|---|---|---|
| Cell Lines* | A/Ser | G/Gly | A/G:Ser/Gly |
| Breast cancer | 3 | 2 | 2 |
| Colon cancer | 1 | 0 | 0 |
| Kidney cancer | 0 | 0 | 3 |
| Malignant Melanoma | 3 | 1 | 6 |
| Non-small cell lung cancer | 1 | 3 | 5 |
| Small cell lung cancer | 1 | 1 | 0 |
| Lymphocytes (EBV) | 2 | | 2 |
| Totals | 11 | 10 | 18 |

TABLE 4

| Genotype at position 2387 | | |
|---|---|---|
| G | A | G/A |
| 24 | 1 | 8 |

*Note: Tumor cell lines are not ideal for assessing allele frequencies in a population because there may be under representation of allelic diversity due to loss of heterozygosity. We used tumor cell lines only because they were readily available at the time the studies were being performed.

These results show that the transferrin receptor is expressed in multiple allelic forms and that the alternate alleles are widely distributed in the population. Over half of the samples analyzed were heterozygous at one or both variable nucleotide positions. Thus, human genes vital for cell growth can be polymorphic, including variation manifested at the protein level. The next step is to produce inhibitors of transferrin receptor specific for each of the allelic forms. In the case of the nucleotide 687 polymorphism, the inhibitor could be directed to DNA, RNA or protein while only DNA or RNA allele specific inhibition is possible for the nucleotide 2387 polymorphism.

Materials and Methods

Materials

Cell lines were obtained from several sources, including the American Type Culture Collection (ATCC). "ATCC Catalogue of Cell Lines & Hybridomas," 7th edition, 1992, ATCC 12301 Parklawn Drive, Rockville, Md. 20852–1776. Cell lines were also obtained from The Coriell Institute for Medical Research, 401 Haddon Avenue, Camden, N.J. 08103 (described in their "1992/1993 Catalog of Cell Lines"), and from Dr. Frank Haluska (MIT Center for Cancer Research) and Dr. Vincent Stanton (formerly of MIT Center for Cancer Research, now at K.O. Technology). All enzymes were purchased from New England Biolabs, except Taq polymerase, which was purchased from Perkin Elmer. dNTPs were purchased from Pharmacia. $\alpha^{32}$PdCTP and $\gamma^{32}$PATP were purchase from New England Nuclear and MDE gel solution was purchased from AT Biochem, Malvern, Pa.

Methods

Cell Culture

Tumor Cells were grown in DME supplemented with calf serum or fetal bovine serum. Lymphocytes were grown in RPMI 1640 supplemented with calf serum. Tissue culture was performed using standard techniques. (I. R. Freshney, "Culture of Animal Cells: A Manual of Basic Technique," Alan R. Liss, Inc., N.Y., N.Y. (1983)).

RNA Isolation

RNA was extracted by suspension of cells in guanidinium isothiocyanate followed by centrifugation through 5.7 M CsCl as described on pages 7.19–7.22 of Sambrook, Fritsch & Maniatis "Molecular Cloning, A Laboratory Manual," Cold Spring Harbor Laboratory Press, Cold Spring Harbor, N.Y. (1989).

cDNA Preparation cDNA was prepared from 1–5 $\mu$g of RNA in 13 $\mu$l of diethylpyrocarbonate (DEPC) treated water using the following protocol from Bethesda Research Labs (BRL) SuperScript kit: 1) 1 $\mu$l of random hexamer solution was added to the tube and mixed gently. 2) The solution was heat to 70° C. for 10 minutes and then incubated on ice for 1 minute. 3) The following were then added: 2 $\mu$l 10×Synthesis buffer, 1 $\mu$l 10 mM dNTP mix, 2 ml 0.1 M DTT, 1 $\mu$l BRL Superscript II reverse transcriptase (200U/$\mu$l). 4) Mix gently and incubate at room temperature for 10 minutes. 5) Transfer tube to a 42° C. block or water bath and incubate for 50 minutes. 6) The reaction was terminated by incubating the tube at 70° C. for 15 minutes, then placed on ice. 7) 1 $\mu$l of RNase H was added to the tube and incubated at 37° C. for 20 minutes.

PCR Amplification of cDNA with TFRC Primers

Nucieotides 501–2561 of TFRC were amplified in 10 separate PCR reactions. The primer coordinates and sizes of the overlapping PCR products are shown in the Table above. For body labelling, each PCR reaction was set up in a 10 $\mu$l volume with the following ingredients: 1 $\mu$l of cDNA, 1 $\mu$l of 10×PCR buffer (15 mM MgCl$_2$, 100 mM Tris-HCl (pH 8.4), 500 mM KCl, 0.1% Gelatin), 1.5 $\mu$l dNTPs (1.25 mM each: dATP, dCTP, dGTP, dTTP), 0.2 $\mu$l primer 1 (any of primers T1, T3, T5, T7, T9, T11, T13, T15, T17 or T19), 0.2 $\mu$l primer 2 (primer T2, T4, T6, T8, T10, T12, T14, T16, T18 or T20 depending on primer 1), 0.25 $\mu$l $\alpha^{32}$PdCTP (3,000 Ci/mMol), 5.7 $\mu$l distilled water, 0.15 $\mu$l Taq DNA Polymerase (2.5 U/$\mu$l). Alternatively, one PCR primer was end labelled by kinasing addition of a radioactive phosphorous to the 5'end with polynucleotide kinase; 0.25 $\mu$l of kinased primer was substituted in place of the $\alpha^{32}$PdCTP in the reaction above. The kinase reaction consisted of 1 $\mu$l oligonucleotide primer (from 20 mM stock), 1 $\mu$l 10×Kinase buffer (as supplied by New England Biolabs), 5 $\mu$l $\gamma^{32}$P ATP (3,000 Ci/mMol), 2.5 $\mu$l distilled water and 0.5 $\mu$l T4 Polynucleotide kinase. Amplification of templates was performed in an MJ Research PTC-100 Programmable Thermal Controller (MJ Research, Waltham, Mass.). Conditions for PCR were: 3 minutes 94° C., followed by 30 cycles consisting of 25 seconds at 94° C., 20 seconds at 45° C., 30 seconds at 72° C. followed by 10 minutes at 72° C.

SSCP Analysis

Radioactively labelled PCR products were diluted into formamide load buffer (95% formamide, 0.5 ×TBE, .0.02% bromophenol blue, 0.02% xylene cyanol) and electrophoresed on 5–10% polyacrylamide gels as described by M. Orita, Y. Suzuki, T. Sekiya and K. Hayashi "Rapid and Sensitive Detection of Point Mutations and DNA Polymorphisms Using the Polymerase Chain Reaction," *Genomics* 5:874–879 (1989). Alternatively, radioactively labelled PCR products were analyzed on Hydrolink MDE Gels using an SSCP protocol supplied by AT Biochem (30 Spring Mill Drive, Malvern, Pa. 19355).

Heteroduplex Analysis

Heteroduplex analysis was performed using Hydrolink, a modified acrylamide manufactured by AT Biochem. Keen, J., Lester, D., Inglehearn, C., Curtis, A. and Bhattacharya, S., "Rapid Detection of Single Base Mismatches as Heteroduplexes on Hydrolink Gels," *Trends in Genetics* 7:5 (1991).

2. Raising Antibodies which Block the Activity of Transferrin Receptor in an Allele-specific Manner Having identified TFRC variation at the protein level, we next sought to raise antisera specific for each of the two variant forms. Such antibodies would constitute allele specific inhibitors capable of arresting growth of tumor cells containing one allele, but not somatic cells from the host containing both alleles. Antibodies that distinguish the serine (Ser) and glycine (Gly) variants of TFRC could be generated by a variety of methods. We chose to first try immunizing rabbits and mice with short peptides corresponding to the Ser and Gly forms of TFRC at residue 142. (A second approach we have undertaken is described below.) We contracted with Peninsula Laboratories (Belmont, Calif.) to synthesize the two peptides shown below. We then coupled these peptides to Bovine Serum Albumin (BSA) or Keyhole limpet hemocyanin (KLH) and immunized rabbits.

See generally Harlow, E. and D. Lane, "Antibodies," Cold Spring Harbor Laboratory Press, Cold Spring Harbor, N.Y. (1988); Coligan, J. E., et al. "Current Protocols in Immunology," Wiley Interscience, New York. (1990). Six rabbits and mice were immunized with the Ser peptide:

$NH_2$-CYS-NLE-LYS-LEU-ASP-SER-THR-ASP-PHE-THR-SER-THR-ILE-LYS-LEU-LEU-ASN-GLU-CYS-COOH  SEQ ID NO. 1 and four rabbits were immunized with the Gly peptide:

$NH^2$-CYS-NLE-LYS-LEU-ASP-SER-THR-ASP-PHE-THR-GLY-THR-ILE-LYS-LEU-LEU-ASN-GLU-CYS-COOH . SEQ ID NO. 2

Each of these peptides contains 3 residues not found in TFRC: Cys residues at either end to facilitate coupling of the peptides to BSA or KLH via the cross-linker sulfo-succinimidyl 4-(maleimidomethyl)cyclohexane-1-carboxylate (sulfo-SMCC), and a non-natural norleucine residue (nle) just after the —NH2 terminal Cys to allow easy assessment of the success of coupling by determination of the nle content of the coupled material. Amino acid analysis of the coupled material (performed by Protein Structure Facility, University of Michigan Medical School, Ann Arbor, Mich.) showed approximately 4 peptides were coupled to each BSA molecule. Mouse immunization schedule was as follows: immunize Balb/c mice with ~15μg of peptide-BSA in 0.5 ml Freund's adjuvant on day 0 (complete adjuvant), 16 (incomplete adjuvant on day 16 and thereafter), 41, 62 and 86, bleed on days 0, 50, 75, and 89 (terminal bleed) and harvest spleens on day 89 for possible fusion to mouse lymphoma cell lines (SP2 or NS1) We contracted with Pel-Freez Biologicals (Rogers, AR) to immunize rabbits according to the following schedule, using 1 mg of antigen in 2 ml of 50% Freund's adjuvant for each immunization:

| Day | Bleeding and Immunization Schedule | |
| --- | --- | --- |
| 0 | PreBleed | Immunize |
| 14 | | Immunize |
| 28 | | Immunize |
| 35 | Bleed | |
| 42 | Bleed | Immunize |
| 49 | Bleed | |
| 56 | Bleed | Immunize |
| 63 | Bleed | |
| 70 | Bleed | |
| 77 | Bleed | |
| 84 | Terminal Bleed | |

Sera from mice and rabbits are tested for immune reactivity specific to either the Ser or Gly form of transferrin receptor. Initially, specific reactivity against the immunizing peptides is evaluated. Two 16 residue peptides identical in sequence to those described above, but without the two terminal Cys residues or the nle residue, were synthesized by SynPep (Dublin, Calif.) and coupled to ovalbumin with glutaraldehyde (see Harlow and Lane, supra). By shortening the peptide, using a different crosslinker, and coupling the antigen to ovalbumin instead of BSA, it is possible to measure only antibodies raised against the relevant segment of the immunizing peptide. Next, the immune sera is evaluated for recognition and binding to immunizing peptide in the presence of blocking peptide (the other allelic form of the receptor). That is, whether sera from a rabbit immunized with Ser peptide can recognize Ser peptide in the presence of an excess of Gly peptide, or whether sera from a rabbit or mouse immunized with Gly peptide can recognize Gly peptide in the presence of an excess of Scr peptide. The allele specific antisera identified by this test are next tested for the same reactivity against the whole transferrin receptor. (Some antisera raised against peptide antigens fail to detect the immunizing peptide when it is part of a larger protein.) If allele specific antibodies are detected against one or both forms of the transferrin receptor, the antibodies are purified by affinity to the immunizing peptide bound to a column in the presence of soluble blocking peptide (i.e., the non-immunizing peptide, which will bind and remove antibodies reactive against both forms of TFRC).

Spleens harvested from the immunized mice or rabbits are used to generate monoclonal antibodies using the recombinant phage antibody system sold by Pharmacia Biotech. McCafferty, et al., Nature, 348:552 (1990). Finally, tumor cells expressing Allele A of the transferrin receptor are incubated with antibodies specific for Allele and tumor cells specific for Allele B are incubated with antibodies specific for Allele B. In both cases, the tumor cells cease proliferating or die due to the antibodies binding to the specific allele, which interferes with the transferrin receptor function. Heterozygous tumor cells incubated with either of the two allele specific antibodies do not die.

To generate blocking antibodies, the antibodies are chimerized. Therefore, the light chain variable region of the corresponding antibody is fused to the human $C_K$ region and the heavy chain variable region is fused to the human IgD constant region since this region has no effector functions such as complement fixation or binding to Fc-receptors. The chimeric gene constructs for the light and heavy chain are transfected into myeloma cells such as PS/20 (see Coligan et al., supra). This cell line does not synthesize endogenous heavy and light immunoglobulin chains. Chimeric TFRC allele specific monoclonal antibodies are isolated from culture supernatants and after purification are tested in nude mice carrying human tumors which are homozygous for the targeted allele so that it can be ascertained that there are no barriers impeding access of the antibody to the extracellular domain of the TFRC in the membrane of the tumor cells in vivo.

Strategies to identify allele specific inhibitors at the DNA or RNA levels for either the nucleotide 687 or 2387 polymorphisms are based on previously described approaches to antisense therapeutics as described, for example, in Toulme and Helene, "Antimessenger oligodeoxyribonucleotides; an alternative to antisense RNA for artificial regulation of gene expression—a review," Gene, 72:51–58 (1988) and Inouye, Antisense RNA; its functions and application in gene regulation—a review," Gene, 72:25–34 (1988). For an account of successful allele specific antisense suppression of a mutant Harvey ras gene see, Monia, et al., "Selective Inhibition of Mutant Ha-ras mRNA Expression by Antisense Oligonucleotides," J. Biol. Chem., 267: 19954 (1992). For a description of ribozyme based strategy see, Gerlach and Young in Chapter 8, "Ribozymes for the Control of Gene Activity in vivo," from Antisense Nucleic Acids and Proteins: Fundamentals and Applicaitons, edited by J. N. M. Mol & A. R. van der Drol. Marcel Kekker, Inc. New York (1990); Cotten and Birnstiel, "Ribozyme mediated destruction of RNA in vivo," EMBO J., 8:3861–3866 (1989); and Cameron and Jennings, "Specific gene suppression by engineered ribozymes in monkey cells," PNAS USA, 86:9139–9143 (1989).

3. Alternate Strategy for Generation of Allele Specific Anti-transferrin Antibodies A second approach we are undertaking is to generate allele specific antibodies in mice using a different strategy.

This approach requires making two mouse strains, each transgenic for one of the two allelic forms of human transferrin receptor (serire or glycine at residue 142). Transgenic mice which have integrated the serine or glycine allele of human TFRC in their genome will be identified by Southern blot analysis using human TFRC receptor specific DNA probes and by PCR analysis using TFRC specific oligonucleotide primers. Expression of human TR receptor on the cell surface of lymphocytes will be tested by indirect immune staining using monoclonal human transferrin specific antibodies as first antibodies and Fluorescein labeled anti murine antibodies as second antibodies. After confirmation of the expression of the two allelic forms of human TR on the surface of murine lymphocytes, we will immunize the transgenic mice expressing the serine 142 allelic form of human TR with lymphocytes derived from transgenic mice expressing the glycine allele of human TR. The only difference between the two transgenic mice is the one amino acid difference in the human TR. The immunization of these mice should therefore elicit an immune response against the glycine epitope of human TR. In order to obtain TFRC serine specific antibodies we will immunize transgenic mice expressing the amino acid 142 glycine allelic form of human TR with lymphocytes derived from serine 142 transgenic mice. After repeated immunization of the two transgenic mice with the two immunogens, we will generate monoclonal antibodies by hybridoma technology or the phage display method. The phage display method will be used to clone those variable region genes which show the highest affinity to lymphocytes derived from the two transgenic animals. In a later step, the light chain variable region genes will be fused to $C_k$ and the heavy chain variable region gene to the immunoglobulin delta constant region. Alternatively, we can express them as antibody fragments without the constant region domains.

Methods

Transgenic mice will be made by microinjecting Ser or Gly specific cDNA expression constructs into mouse eggs of the same inbred mouse strain. For higher expression in the transgenic mice, an intron DNA sequence can be added. For B cell specific expression, we can use an immunoglobulin promoter or, for T cell scientific-expression, we can use the θ or theta promoter, for example. Alternatively, we can use the CMV promoter as a ubiquitously expressing promoter.

4. Efficacy Testing on Human Cells

The identified allele-specific inhibitors Must be tested for their ability to inhibit transferrin receptor activity in normal human cell lines of appropriate genotype such as fibroblasts or EBV transformed lymphoblastoid cell lines.

The allele specific antibodies or antisense constructs or other inhibitors will be tested for their ability to inhibit transferrin receptor activity in well known tumor cell lines of the appropriate genotype, especially those known to undergo frequent LOH at the transferrin receptor locus, such as small cell lung cancer, renal cancer, non small cell lung cancer, cervical carcinomas, and breast cancer. The genotype of these tumor cell lines at the TFRC locus is determined. To genotype the tumor cells, RNA or genomic DNA is extracted, the relevant region of the gene is amplified by PCR from cDNA or DNA assayed by an RFLP technique (Mspl or BsoFl digestion), by SSCP, by oligonucleotide hybridization, or by direct sequencing to determine the genotype. Those which are homozygous for the appropriate allele are screened for transferrin receptor inactivation and consequent arrest of cell division by the various allele-specific inhibitors.

5. Human Clinical Trials

Patients with tumors known to delete one copy of chromosome 3 (resulting in LOH at the transferrin receptor locus) are candidates for treatment with the antibody inhibitors of this invention. Patients appropriate for treatment with a specific inhibitor can be identified by a two step genetic screening test requiring a blood sample and, for constitutionally heterozygous patients, a small sample of the patient's tumor. The first part of the test requires only blood (or any other source of nonmalignant somatic cells). The patient's allelic status (genotype) at nucleotides 687 and 2387 of TFRC is determined by PCR amplification of DNA segments surrounding each of the polymorphic sites followed by allele specific oligonucleotide hybridization or restriction endonuclease digestion with Mspl (to determine genotype at 687) or BsoFl (to determine genotype at 2387). A tumor biopsy is obtained only from patients heterozygous at position 687 or 2387 or both. The method for determination of the tumor genotype depends on the amount of tumor DNA available. If $\geq 5$ μg is available the DNA will be digested with Mspl or BsoFl as appropriate, electrophoresed on an agarose or polyacrylamide gel, blotted and hybridized with the suitable TFRC fragment. Southern blotting allows absolute quantitation of allele dosage. If <5 μg of tumor is available the genotype is assayed by a PCR based method such as SSCP which is adapted for quantitative studies. Once patients with appropriate genotypes have been identified the responsiveness of their tumor cells to the targeted inhibitors is assayed in tissue culture. First, cell cultures of the tumor and of normal lymphocytes can be established. These cultures are then treated (screened) with the appropriate allele-specific inhibitors of transferrin receptor. A therapeutically effective inhibitor is one which kills the tumor cell line, while permitting growth of the lymphocyte-derived line, (the patient's normal cells), albeit possibly slower growth. An allele-specific antibody which differentiates between tumor and normal cells is then administered therapeutically to the patient.

EXAMPLE C

Dihydrofolate Reductase (DHFR)

As described above the DHFR gene encodes a protein essential for cell proliferation. Inhibitors of DHFR, particularly, methotrexate (MTX), are widely used in cancer chemotherapy. currently the most widely used antifolate in cancer therapy.

The DHFR gene has been cloned and its cDNA sequence has been determined several times. (Morandi et al., "Multiple Forms of Human Dihydrofolate Reductase Messenger RNA," *J. Mol. Bios*, 156:583–607 (1982); Masters and Attardi, The nucleotide sequence of the cDNA coding for the human dihydrofolic acid reductase," *Gene*, 21:59–63 (1983); Masters et al., "A Human Dihydrofolate Reductase Pseudogene and Its Relationship to the Multiple Forms of Specific Messenger RNA," *J. Mol. Bio.*, 167:23–36 (1983)). The gene is located on chromosome 5q11.2-q13.2, a region frequently reduced to homozygosity in colorectal cancer and in liver cancer. We subdivided the cDNA sequence, which comprises 979 bp into 5 overlapping fragments. The fragments were generated by PCR using 10 specific oligonucleotides (D1-D10) and the same cDNAs used for the human transferrin receptor study described above. The PCR fragments, between 219 bp and 263 bp in length, were analyzed by SSCP analysis as described in Example B. The oligonucleotides used were:
D1: 5'-GAGGTCCTCCCGCTGCTGTC-3'SEQ ID NO. 3
D2: 5'-CTTGAGTTCTCTGCTGAGAAC-3'SEQ ID NO. 4
D3: 5'-CATTCCTGAGAAGAATCGACC-3'SEQ ID NO. 5
D4: 5'-GTCTTGCATGATCCTTGTCAC-3'SEQ ID NO. 6
D5: 5'-GAAGCCATGAATCACCCAG-3'SEQ ID NO. 7
D6: 5'-CTTAAACTAGAAAACACCTTC-3'SEQ ID NO. 8
D7: 5'-GTACAAATTTGAAGTATATG-3'SEQ ID NO. 9
D8: 5'-GGTCTTGGAAAGCACTTAG-3'SEQ ID NO. 10
D9: 5'-CATTTATGAGACATTCTTGC-3'SEQ ID NO. 11
D10: 5'-GCTTTTGGTATTTCCACTAG-3'SEQ ID NO. 12

The radiolabelled PCR products were analyzed on a nondenaturating acrylamide gel ±10% glycerol. We identified two DNA polymorphisms, at nucleotide 721 and 829 (numbering of nucleotides from Genbank, accession number J00140). Three of 22 tested cDNAs were heterozygous for T or C at nucleotide 829. The other 19 cDNAs were homozygous for C. At nucleotide 721, four of 20 cDNAs were heterozygous for A or T. 16 other cDNAs were homozygous for T. These nucleotide substitutions, which do not result in an amino acid exchange, are ideal targets to develop antisense oligonucleotides or ribozymes which will specifically discriminate between the different polymorphisms.

Although the foregoing invention has been described in some detail by way of illustration and example for purposes of clarity of understanding, it will be obvious to one skilled in the art that certain changes and modifications may be practiced within the scope of the appended claims.

What is claimed is:

1. A method for identifying a patient suitable for treatment with an allele-specific inhibitor, comprising the steps of:
   a) identifying a patient whose somatic cells are heterozygous for a gene essential for cell viability or growth; and
   b) determining whether cancer cells of said patient are homozygous for said gene;
   wherein homozygosity of said cancer cells for said gene is indicative that said patient is suitable for said treatment.

2. The method of claim 1, wherein said identifying comprises determining the genotype of said patient at polymorphic sites in said gene in somatic cells.

* * * * *